United States Patent
Palmqvist et al.

(10) Patent No.: US 11,160,699 B2
(45) Date of Patent: Nov. 2, 2021

(54) ABSORBENT ARTICLE

(71) Applicant: Essity Hygiene and Health Aktiebolag, Gothenburg (SE)

(72) Inventors: Lisa Palmqvist, Gothenburg (SE); Anna Knös, Gothenburg (SE); Philip Blomström, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 0 days.

(21) Appl. No.: 15/734,388

(22) PCT Filed: Jun. 15, 2018

(86) PCT No.: PCT/SE2018/050630
§ 371 (c)(1),
(2) Date: Dec. 2, 2020

(87) PCT Pub. No.: WO2019/240642
PCT Pub. Date: Dec. 19, 2019

(65) Prior Publication Data
US 2021/0169711 A1 Jun. 10, 2021

(51) Int. Cl.
*A61F 13/84* (2006.01)
*A61F 13/15* (2006.01)

(52) U.S. Cl.
CPC .... *A61F 13/8405* (2013.01); *A61F 13/15577* (2013.01); *A61F 2013/8452* (2013.01)

(58) Field of Classification Search
CPC .......... A61F 13/8405; A61F 13/15577; A61F 2013/8452; A61F 2013/00187;
(Continued)

(56) References Cited

U.S. PATENT DOCUMENTS 6,207,738 B1 3/2001 Zuckerman et al.
6,551,607 B1 4/2003 Minerath, III et al.
(Continued)

FOREIGN PATENT DOCUMENTS

CN 1471595 A 1/2004
CN 1694669 A 11/2005
(Continued)

OTHER PUBLICATIONS

International Preliminary Report on Patentability (Form PCT/IPEA/416) and (Form PCT/IPEA/409) dated Sep. 14, 2020, issued by the European Patent Office, in the corresponding International Application No. PCT/SE2018/050633. (12 pages).
(Continued)

*Primary Examiner* — Adam Marcetich
(74) *Attorney, Agent, or Firm* — Buchanan Ingersoll & Rooney PC

(57) ABSTRACT

The absorbent article comprises at least a topsheet layer and a backsheet layer, each layer having a body facing surface and a garment facing surface, and longitudinal and transversal edges, the article having a longitudinal front portion, a longitudinal back portion and a crotch portion located between the front and the back portion. The article comprises a first and a second zone of microencapsulated phase change material on a surface of a layer of the article. The first and second zones are selected form zones having different microencapsulated phase change materials, different concentrations of a microencapsulated phase change material or comprise microencapsulated phase change material having different phase change temperature intervals.

32 Claims, 3 Drawing Sheets

(58) Field of Classification Search
CPC .......... A61F 13/046; A61F 2013/15146; A61F 13/42; A61F 2013/421; A61F 2013/422; A61F 2013/425; A61F 2013/426; A61F 2013/51059; A61F 2013/51061; A61F 2013/51064; A61F 2013/51066; A61F 2013/51069; A61F 2013/51071; A61F 2013/51073; A61F 2013/51076
See application file for complete search history.

(56) References Cited

U.S. PATENT DOCUMENTS

| | | | |
|---|---|---|---|
| 10,316,234 B2 | 6/2019 | Mason | |
| 2003/0106605 A1* | 6/2003 | Jameson | B41J 2/04 141/98 |
| 2003/0109816 A1* | 6/2003 | Lachenbruch | A61F 13/0213 602/2 |
| 2003/0114812 A1* | 6/2003 | Braverman | A61F 13/4755 604/367 |
| 2003/0195448 A1* | 10/2003 | Jensen | A61F 13/0203 602/41 |
| 2004/0102750 A1* | 5/2004 | Jameson | A61F 13/511 604/367 |
| 2004/0127872 A1 | 7/2004 | Petryk et al. | |
| 2004/0127883 A1 | 7/2004 | Cowell et al. | |
| 2005/0256478 A1* | 11/2005 | Genke | A61F 13/51405 604/385.01 |
| 2007/0151261 A1* | 7/2007 | Roberts | F25D 5/02 62/4 |
| 2008/0091162 A1 | 4/2008 | Maldonado et al. | |
| 2008/0206529 A1 | 8/2008 | Ueminami et al. | |
| 2008/0208154 A1 | 8/2008 | Oetjen et al. | |
| 2008/0233368 A1* | 9/2008 | Hartmann | D06M 23/12 428/206 |
| 2009/0155325 A1* | 6/2009 | Wenzel | A61L 15/34 424/402 |
| 2009/0288259 A1* | 11/2009 | Lean | B29C 44/22 5/740 |
| 2010/0121304 A1* | 5/2010 | Zhou | A61F 13/82 604/387 |
| 2011/0146900 A1 | 6/2011 | Ruman | |
| 2012/0089106 A1 | 4/2012 | Komatsu et al. | |
| 2012/0193572 A1* | 8/2012 | MacKay | B29C 44/3446 252/78.1 |
| 2012/0242009 A1 | 9/2012 | Mullane et al. | |
| 2013/0261586 A1* | 10/2013 | Lee | A61F 13/4755 604/385.01 |
| 2014/0054827 A1* | 2/2014 | Mullane | A61F 13/15731 264/405 |
| 2015/0106992 A1* | 4/2015 | Blakely | A41D 13/0056 2/69 |
| 2015/0257943 A1* | 9/2015 | Noel | A61F 13/472 604/369 |
| 2015/0282998 A1* | 10/2015 | Arizti | A61F 13/15707 604/385.101 |
| 2015/0282999 A1 | 10/2015 | Arizti et al. | |
| 2016/0008237 A1 | 1/2016 | Goldstein et al. | |
| 2016/0166074 A1* | 6/2016 | Rose | A47G 9/0253 5/636 |
| 2017/0135877 A1 | 5/2017 | Kudo et al. | |
| 2017/0360620 A1* | 12/2017 | Cree | A61F 13/51121 |
| 2018/0140116 A1* | 5/2018 | Werner | A47G 9/0253 |
| 2019/0001017 A1 | 1/2019 | Palmqvist et al. | |
| 2019/0300770 A1* | 10/2019 | Nomura | C09K 5/063 |

FOREIGN PATENT DOCUMENTS

| | | |
|---|---|---|
| CN | 102827573 A | 12/2012 |
| CN | 102827582 A | 12/2012 |
| CN | 103349591 A | 10/2013 |
| CN | 103374334 A | 10/2013 |
| CN | 103374335 A | 10/2013 |
| CN | 103374336 A | 10/2013 |
| CN | 204379555 U | 6/2015 |
| CN | 107090075 A | 8/2017 |
| CN | 107735112 A | 2/2018 |
| EP | 3162334 A1 | 5/2017 |
| KR | 20050016837 A | 2/2005 |
| KR | 20060110492 A | 10/2006 |
| KR | 20060110495 A | 10/2006 |
| RU | 2244565 C2 | 1/2005 |
| RU | 2385168 C1 | 3/2010 |
| RU | 2540596 C2 | 2/2015 |
| WO | 0069483 A1 | 11/2000 |
| WO | 02-24992 A1 | 3/2002 |
| WO | 2004060244 A1 | 7/2004 |
| WO | 2007064258 A1 | 6/2007 |
| WO | 2009105740 A2 | 8/2009 |
| WO | 2010042470 A1 | 4/2010 |
| WO | 2011056777 A1 | 5/2011 |
| WO | 2017002503 A1 | 1/2017 |
| WO | 2017007398 A1 | 1/2017 |
| WO | 2017218052 A1 | 12/2017 |

OTHER PUBLICATIONS

International Search Report (PCT/ISA/210) dated Mar. 15, 2019, by the European Patent Office as the International Searching Authority for International Application No. PCT/SE2018/050630.
International Search Report (PCT/ISA/210) dated Mar. 15, 2019, by the European Patent Office as the International Searching Authority for International Application No. PCT/SE2018/050633.
International Search Report (PCT/ISA/210) dated Mar. 15, 2019, by the Sweden Patent Office as the International Searching Authority for International Application No. PCT/SE2018/050631.
Written Opinion (PCT/ISA/237) dated Mar. 15, 2019, by the European Patent Office as the International Searching Authority for International Application No. PCT/SE2018/050630.
Written Opinion (PCT/ISA/237) dated Mar. 15, 2019, by the European Patent Office as the International Searching Authority for International Application No. PCT/SE2018/050633.
Written Opinion (PCT/ISA/237) dated Mar. 15, 2019, by the Sweden Patent Office as the International Searching Authority for International Application No. PCT/SE2018/050631.
International Preliminary Report on Patentability (Form PCT/IPEA/416 and Form PCT/IPEA/409) dated Aug. 3, 2020, issued by the European Patent Office, in the corresponding International Application No. PCT/SE2018/050630.
First Office Action dated Apr. 12, 2021, by the Chinese Patent Office in corresponding Chinese Patent Application No. 201880094282.2, and an English Translation of the Office Action. (19 pages).
Office Action (Decision to Grant) dated May 24, 2021, by the Russian Patent Office in Russian Patent Application No. 2021100039, and an English Translation of the Office Action. (18 pages).
Office Action (Question, Arguments, Objection, Proposals) dated May 27, 2021, by the Russian Patent Office in Russian Patent Application No. 2021100041, and an English Translation of the Office Action (13 pages).
Office Action (Decision to Grant) dated Jun. 10, 2021, by the Russian Patent Office in Russian Patent Application No. 2021100038, and an English Translation of the Office Action. (19 pages).
First Office Action dated Jul. 14, 2021, by the Chinese Patent Office in corresponding Chinese Patent Application No. 201880094215.0, and an English Translation of the Office Action. (15 pages).
Supplemental Notice of Allowability dated Aug. 12, 2021, by the U.S. Patent and Trademark Office in U.S. Appl. No. 15/734,279.

* cited by examiner

ABSORBENT ARTICLE

TECHNICAL FIELD

The present disclosure pertains to an absorbent article, such as a sanitary napkin, a panty liner, an incontinence pad, an incontinence diaper, a belted diaper, or a baby diaper, comprising a microencapsulated phase change material (PCM). The disclosure further pertains to a method for producing such an absorbent article as well as an array of absorbent articles.

BACKGROUND

Absorbent articles for personal hygiene are designed to absorb and contain body exudates. The absorbent articles normally comprise a topsheet layer facing the user, a backsheet layer facing the garment of a user and optionally an absorbent core located between these layers.

Absorbent articles may contain additives to provide certain advantages for the user. KR20060110492 discloses a diaper comprising microencapsulated phase change material distributed in the absorbent core to suppress a temperature rise of the infant scrotum.

SUMMARY

The present disclosure is based on the insight how an absorbent article may be adapted for specific user requirements to thereby optimize the performance of the article for the user.

Thus, the absorbent article comprises at least a topsheet layer and a backsheet layer, each layer having a body facing surface and a garment facing surface, and longitudinal and transversal edges, the article having a longitudinal front portion, a longitudinal back portion and a crotch portion located between the front and the back portion. The article comprises a first and a second zone of microencapsulated phase change material on a surface of a layer of the article. The first and second zones are selected form zones having different microencapsulated phase change materials, different concentrations of a microencapsulated phase change material or comprising microencapsulated phase change material having different phase change temperature intervals.

The article may comprise a first and a second zone of microencapsulated phase change material on the same surface of a layer of the article.

The first zone may be more than 0% and less than 100% of the surface area of the layer, such as 1-99%, such as 10-90%. The second zone may be more than 0% and less than 100%, such as 99-1%, such as 90-10% of the surface area of the layer.

The first phase change material may have a phase change transition temperature within 10-50° C., such as 10-40° C. The second zone of microencapsulated phase change material may have a phase change transition temperature within 10-50° C., such as 10-40° C.

The first zone may be at least partly surrounded by the second zone of microencapsulated phase change material.

The first and second zones may be at least partly overlapping.

The second zone may form a micropattern within at least a part of the first zone.

The article may comprise a plurality of zones of microencapsulated PCM.

The microcapsules may be of a permanent, non-breakable and non-water-soluble type.

The concentration of PCM in the zones may be >0.01<17 $g/m^2$.

The concentration of microcapsules in the first zone may be 0.01-17 $g/m^2$, such as 0.01-10 $g/m^2$, such as 0.01-5 $g/m^2$. The concentration of microcapsules in the second zone may be 0.01-17 $g/m^2$ such as 0.01-10 $g/m^2$, such as 0.01-5 $g/m^2$.

The first zone may be in the wetness zone. The second zone may be outside the wetness zone, but inside the crotch portion of the article.

The phase change material may be a reversible temperature regulating phase change material.

The microencapsulated phase change material may be located on any of the surfaces of the topsheet layer. The article may further comprise an intermediate layer having a body facing surface and a garment facing surface and wherein the microencapsulated phase change material may be located on any of these surfaces. The microencapsulated phase change material may be in the core layer.

The absorbent article may be selected from a sanitary napkin, a panty liner, an incontinence pad, an incontinence diaper, a belted diaper, and a baby diaper.

The method entails applying PCM to an absorbent article comprising at least a topsheet layer and a backsheet layer, each layer having a body facing surface and a garment facing surface and longitudinal and transversal edges, the article having a longitudinal front portion, a longitudinal back portion and a crotch portion located between the front and the back portion. The method, comprising the steps of printing a first and a second zone of microencapsulated phase change material on a surface of a layer of the article, wherein the first and second zones are selected form zones having different microencapsulated phase change materials, different concentrations of a microencapsulated phase change material or comprise microencapsulated phase change material having different phase change temperature intervals.

Printing may be by means of an in-line synchronized print technique, such as a flexographic printing technique.

An array of absorbent articles comprising a first absorbent article comprising at least a topsheet layer and a backsheet layer, each layer having a body facing surface and a garment facing surface, and longitudinal and transversal edges, the article having a longitudinal front portion, a longitudinal back portion and a crotch portion located between the front and the back portion, the article comprises a first zone of microencapsulated phase change material on a surface of a layer of the article; a second absorbent article comprising at least a topsheet layer and a backsheet layer, each layer having a body facing surface and a garment facing surface, and longitudinal and transversal edges, the article having a longitudinal front portion, a longitudinal back portion and a crotch portion located between the front and the back portion, the article comprises a second zone of microencapsulated phase change material on a surface of a layer of the article; wherein the first and second zones are selected from zones having different microencapsulated phase change materials, different concentrations of a microencapsulated phase change material or comprising microencapsulated phase change material having different phase change temperature intervals.

DETAILED DESCRIPTION OF THE PREFERRED EMBODIMENTS

Figure 1A:
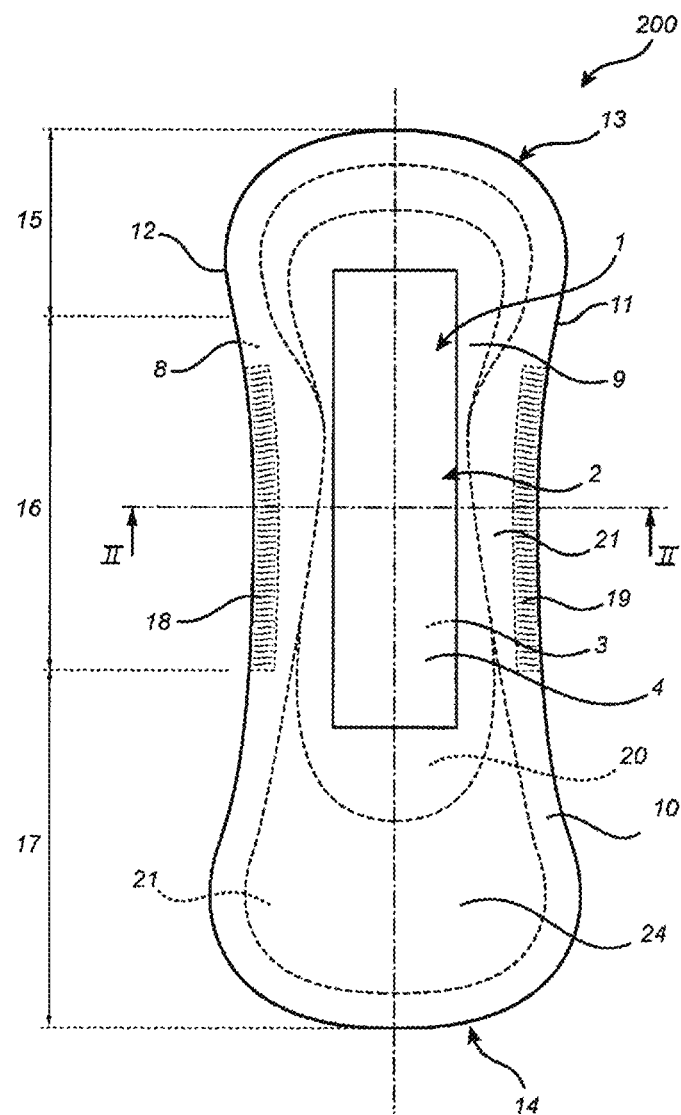
FIG. 1A is a top view of an incontinence pad according to a preferred embodiment.

A zone is an area which may the same on every product and thus may be synchronized to the shape of the article. A zone may thus be distinguished from a continuous string, sheet or line in any pattern.

Zones may be functional zones on the product in which the PCM is precisely located through printing to give optimal performance of the additive on the product i.e. where the substance will be most effective e.g. in the most beneficial part of the product.

The zone may be discrete with boundaries starting and ending within the edge borders of the layer. The boundary of the zone may end at least 1 mm from the transversal edges of the layer. The boundary of the zone may end at least 1 mm from the longitudinal edges of the layer.

A first zone may form a micropattern within a second zone. A first and a second zone may be at least partly overlapping. There may be a plurality of zones of microencapsulated PCM.

A zone may have a boundary enclosing an area of at least 1 $mm^2$, or at least 5 $mm^2$. The first zone may be more than 0% and less than 100% of the surface area of the layer. The second zone may be more than 0% and less than 100% of the surface area of the layer.

The microencapsulated PCM may be applied on 1-100% of a surface area of a layer of the article, such as 1-90%, such as more than 1% and less than 90%, or more than 1% and less than 80%.

At least the first zone may have a rounded shape. The rounded shape of the zone may include a circular shape, an elliptic shape, a rectangular shape and a square shape with rounded corners. At least the first zone may have its center point in the crotch portion of the article.

The size of the microcapsules may be at least 1 µm, or at least 3 µm, or at least 10 µm and may be below 100 µm, or below 70 µm, or below 30 µm. The size of the microcapsules may be 1-100 µm, or 1-70 µm, or 10-50 µm.

The concentration of microcapsules on the surface of the layer may be at least 0.01 $g/m^2$, or at least 0.05 $g/m^2$ or at least 0.1 $g/m^2$ or at least 0.5 $g/m^2$ and below 17 $g/m^2$, or below 10.0 $g/m^2$ or below 5 $g/m^2$. The concentration of microcapsules on the surface of the layer may be 0.01-17 $g/m^2$, or 0.01-10 $g/m^2$ or 0.01-5 $g/m^2$.

The concentration of PCM in the zones may be >0.01<17 $g/m^2$.

The article comprises a first and second zone of microencapsulated PCM. The first and second zones are selected form zones having different microencapsulated phase change materials, different concentrations of a microencapsulated phase change material or comprising microencapsulated phase change material having different phase change temperature intervals, or combinations thereof.

The article may comprise a first and a second zone of microencapsulated phase change material on different layers of the article. The article may comprise a first and a second zone of microencapsulated phase change material on the same surface of a layer of the article. The article may comprise a first and a second zone of microencapsulated PCM on different surfaces of a layer of the article. In an array there may be a first and a second zone of microencapsulated phase change material on different articles.

The concentration of microencapsulated PCM in the first zone may be 0.01-17.0 $g/m^2$. The concentration of microencapsulated PCM in the second zone may be 0.01-17.0 $g/m^2$. The concentration ranges applicable for the first and second zones may be the same. However, according to the present disclosure the concentration of the PCM in the absorbent article may differ between the first and second zones within the range 0.01-17.0 $g/m^2$.

The first phase change material may have a phase change transition temperature within 10-50° C., such as 10-40° C. The second zone of microencapsulated phase change material may have a phase change transition temperature within 10-50° C., such as 10-40° C. The temperature ranges applicable for the first and second zones may be the same as disclosed herein, but the individual ranges of the first and second zones differ between the zones but within this broader range, when applied in the absorbent article.

The capsule material of the microcapsules may be of a non-water-soluble material as known to the skilled man in the art. The capsule material may be of a non-water-soluble polymer material such as polymethyl methacrylate, polystyrene, polyethylene, polyurethane, urea/formaldehyde, melamine/formaldehyde, or inorganic such as calcium carbonate, silica or sodium silicate as known to the man skilled in the art. Natural polymers such as gelatin may also be used as shell materials provided they have low water solubility and melting points above the temperature range of the PCM activity.

The microcapsules may be of a permanent type, i.e. that do not break up during use. Mechanical strength may be important to keep the PCMs intact to avoid leakage and keep the temperature controlling performance. The capsules may need to have sufficient mechanical strength to endure shear forces that may be applied by a moving body during use of the product to avoid leakage of PCM material from the capsules. The urea-formaldehyde system is an example of polymeric shell material that may be tailored to give high shear strength and low leakage. The shell structure is permanent in contrast to capsules for long-lasting or time-release type of claims where the shell should have low enough strength to break upon pressure or friction from the human body to release the core substance. The activation of the microcapsules may be performed by activation upon contact. Not all microcapsules will be activated at the same time as some may be buried further down in the material and there will thus be a slow, continuous and beneficial activation during use of the article. A long-lasting effect can thus be achieved.

The phase change material, i.e. the core material of the microcapsules, may be a reversible temperature regulating phase change material which may revert to its original form. An advantage is the possibility to create an active climate control on demand when needed. In comparison to for example menthol/menthol derivatives which gives a cooling effect regardless of temp, PCM is only cooling at certain temperature ranges and may in addition also emit heat.

Normal skin temperatures are about 31-34° C. for legs and thighs and about 34-37° C. for abdomen. However, in these regions an increased temperature above normal body temperature is also likely to happen when a person moves heavily such as during sports, or is present in a hot environment and in certain climates. Thus, the temperature in different regions of the skin and body differs. For example, the skin in the intimate area closest to the thighs may have a temperature a few degrees higher than that of the skin on the lower thighs due to the enclosed location. Sweat may first increase the temperature and then decrease it when the heat of evaporation makes the sweat fluid cooler. This may be balanced by an area with encapsulated PCM materials. In the center of a hygiene product, where warm fluids such as urine or menstrual blood will warm up and then cool down the product and thus the adjoining skin or membrane, a zone with microencapsulated PCM within a phase change temperature range corresponding to the warm body fluid may be beneficial to balance the temperature variations for increased, more stable, thermal comfort. The waist area of a baby or adult diaper may accommodate warm and humid conditions better if an encapsulated PCM material is added to the waist zone. According to the present disclosure temperature variations may conveniently be alleviated.

The microencapsulated PCM may have a phase change transition temperature to provide a cooling sensation The PCM material for the microcapsules may be a non-volatile organic temperature regulating agent such as paraffin wax mixtures or polymers such as polyethylene glycols, fatty acids or ester derivatives of these (such as caprylic, capric, lauric and tridecylic acid and eutectic mixtures of these with palmitic, myristic or stearic acid) as well as polyalcohols, derivatives thereof and polyethylenes, or they may be an inorganic such as salt hydrates e.g. hydrated calcium and magnesium chlorides or hydrated carbonates. Examples of commercial producers of micro encapsulated PCMs suitable for body wear applications or energy storage applications in the comfort temperature interval for humans are Devan Chemicals (BE), Microtek Laboratories (US), Climator (SE) and MicroCaps (SLO).

Examples of different microencapsulated PCMs to include in the first and second zones are n-alkanes of different chain lengths such as n-octadecane with a phase change temperature interval around 28-32° C. and n-nonadecane with a phase change temperature interval around 32-34° C. Another system may be n-heptadecane, 20-26° C. and n-eicosane, 36-37° C.

The microencapsulated PCM may be printed on a layer of the absorbent article as a composition being a dispersion of the PCM in water or mixed with aqueous binder solution or mixed with a water-based printing ink.

The PCM composition is applied by printing on the absorbent article. By printing we herein mean a precise application of a fluid to form a coating or other dry layer on a substrate. By precise we mean that the medium will be placed in designated zones on the substrate, rather than in a poorly controlled fashion such as when using a spraying, coating or extrusion technique. The print may be of contact type such as selected from flexoprint, screen print, offset, rotogravure or of non-contact type, such as selected from digital inkjet which may be continuous or drop on demand, intermittent drop formation by piezo, heat activated or other type of technology.

The PCM composition may be applied by an in-line synchronized print technique, allowing for an exact placement of the PCM on the article.

The steps of in-line synchronized printing may be incorporated as steps in a process of manufacturing absorbent articles, or the layers may be in-line synchronized printed before the assembly of the product.

After application of the PCM on the absorbent article it will dry almost instantaneously. However, a drying step may be added, such as blowing hot air on the printed surface.

The PCM composition may be applied in selected areas as desired, and in any desired pattern. The present method allows very accurate zones to be formed.

When arranged in the absorbent article, the top sheet has body facing surface and a garment facing surface. The PCM composition may be applied to one or both of said surfaces. By applying the PCM composition on the body facing surface the user obtains a direct access to the agents. By providing the PCM on a garment facing surface a slower activation and release of the microcapsules are obtained which may be desirable for certain applications. The PCM may also be applied to an intermediate layer of the article.

Depending on the location of the PCM various advantageous functional effects can be obtained. Examples of zones of PCM with different functions are given below. These zones can be used individually, but may of course advantageously be combined to achieve the desired characteristics of the absorbent article.

The PCM composition may be applied in a zone along at least a part of the longitudinal side edges. Further, a zone may be applied in a central part of the article.

The microencapsulated PCM may be applied in a zone of the article selected from:
along longitudinal side edges of the crotch portion;
a central area of the crotch portion;
a central area of the front portion;
a central area of the back portion;
a waist area.

The absorbent article may further comprise a wing extending from each longitudinal side edge of the article and microencapsulated PCM may be applied in a zone on said wings.

The absorbent article comprises at least a topsheet layer and a backsheet layer and optionally an absorbent layer arranged between the topsheet and the backsheet layers.

Each layer of the absorbent article has a garment facing surface and a body facing surface, and the PCM may be applied to any of said surfaces. The PCM may be added to an intermediate layer, such as an acquisition layer, located beneath a topsheet.

The absorbent article may comprise a liquid pervious body facing topsheet of a nonwoven, a film or a laminate thereof or a foam The backsheet material may be breathable or non-breathable film or nonwoven and film laminate. The back sheet is facing away from the user during use, and is opposite to the body facing topsheet layer of the absorbent article. A fastening means may be applied on the garment facing side of the back sheet, which may be covered by a release paper or single wrap. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment. Furthermore, the fastening means may be a mechanical fastener such as hook-type fasteners, clips, press studs, etc. or may be a frictional fastener such as a frictional coating or open-celled foam.

Combinations of different types of fasteners are also conceivable. The fastening means is optional to the invention and may be omitted, if desired.

The absorbent article may comprise a core of absorbent material. The absorbent core may comprise a first and a second absorbent layer. The absorbent layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibers and superabsorbent material, wherein the ratio of superabsorbent material to fibers may vary in the layer. The first and second absorbent layers may have any suitable shape, such as an hourglass shape with widened end portions and a narrow portion in the crotch portion, or a rectangular shape.

The absorbent core may be made up of any suitable absorbent or fluid uptake material as known in the art, such as one or more layers of cellulose fluff pulp, foam, fibre waddings, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. The absorbent core may further incorporate components for improving the properties of the absorbent core. Some examples of such components are binder fibers, fluid-dispersing materials, wetness indicators etc., as known in the art.

The application of the microcapsules by print allows for a precise placement of a delicate printed zone in chosen areas on the article, compared with when the additive is applied for example as a constituent of the spin finish on a topsheet, in a so-called cocktail, which is commonly used by nonwoven suppliers. To further increase the benefits the print may be combined with precise in-line positioning (synchronization) of the print on any product. This enables the print to be placed in exact zones or areas, i.e. particular functional zones of the product. In this way the PCM will be applied only in the printed zones, thus allowing for less amount and possibility for tailor made zones or areas.

Print including one or more of the PCM may be applied in different layers of the product. The topsheet, an intermediate layer, core or acquisition layer, or on a backsheet, glued part, wrap or release paper may be printed. More than one printed area, having the same or different printed additives, are possible on the same layer of the product and on different layers in the product. The printed beneficial zones may be placed within an absorbing area or outside of the absorbing area of an article.

The first and second zones of microencapsulated PCM, selected form zones having different microencapsulated phase change materials, different concentrations of a microencapsulated phase change material or comprising microencapsulated phase change material having different phase change temperature intervals, can be formed on different absorbent articles in an array to accommodate for different needs in terms of temperature regulation.

An array may also comprise at least two absorbent articles each article having at least two zones selected form zones having different microencapsulated phase change materials, different concentrations of a microencapsulated phase change material or comprising microencapsulated phase change material having different phase change temperature intervals.

The disclosure will now be described by way of example of an absorbent pad, referring to the drawings.

Figure 1B:
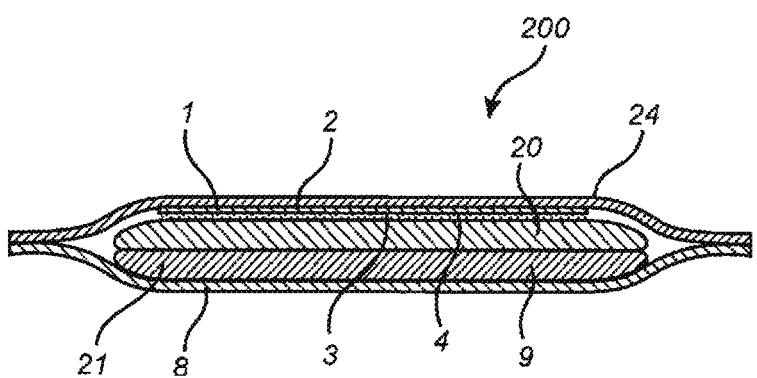
FIG. 1B is a cross-sectional view of the pad in FIG. 1A.

The absorbent article 200 shown in FIGS. 1A and 1B is a urine incontinence protector in the form of a pad. The pad is seen from the side of the pad that is intended to be facing towards a wearer's body when being worn. The pad comprises a liquid permeable topsheet 24, a liquid impermeable backsheet 8, and an absorbent core 9 enclosed between the topsheet 24 and the backsheet 8, and an acquisition and distribution layer 1 arranged between the topsheet 24 and the absorbent core 9.

The topsheet 24 and the backsheet 8 of the pad extend together laterally outside of the absorbent core 9 along the whole circumference of the absorbent core 9 and is connected to each other in an edge joint 10 around the periphery of the absorbent core 9. The topsheet 24 comprises any material which is suitable for the purpose, i.e. soft and liquid pervious.

The backsheet 8 is fluid impermeable. However, backsheet materials that are only fluid repellant may be used particularly in instances where relatively small amounts of urine are expected to be taken up. Furthermore, the backsheet 8 may have an outer, garment-facing surface of a textile material such as nonwoven.

The absorbent core 9 may be made up of any suitable absorbent or fluid uptake material as known in the art, such as one or more layers of cellulose fluff pulp combined with fibers or particles of highly absorbent polymer material.

The pad in FIG. 1A has an elongate, generally rectangular shape when fully extended in all directions. Any suitable shape may be used for the absorbent product, such as hourglass shape, trapezoidal shape, triangular shape an oval shape, etc. The shape of the product of the invention may be symmetrical about a transverse center line through the product, or may be asymmetrical with end portions having differing shapes and/or differing sizes. The pad has two longitudinal side edges 11, 12 extending generally in the same direction as a longitudinal center line through the absorbent product. Front and rear end edges 13, 14 typically extend transversely to the longitudinal center line at the ends of the absorbent product. The rear end edge 14 is intended to be orientated rearwards during use of the absorbent article, and the front-end edge 13 is intended to be facing forwards towards the abdomen of the wearer. The pad has a longitudinal front portion 15, a longitudinal back portion 17 and a crotch portion 16 located intermediate the front and back portions 15, 17. The crotch portion 16 is a portion which is intended to be placed against the crotch of a wearer during use of the product and to constitute the main acquisition area for body fluid that reaches the pad. The pad may further include fastening means for fastening of the absorbent product inside a supporting pant garment, such as a pair of underpants.

Elastic elements 18, 19 may be arranged along the side edges laterally outside the absorbent core 8. The elastic elements 18, 19 may be bands of elastic material. The elastic elements 18, 19 are optional components of the absorbent product and may be omitted.

The acquisition and distribution material 1 in FIG. 1A is situated above the absorbent core 9 and beneath and in direct contact with the topsheet 24 and may be a nonwoven high loft material or a perforated material such as a SMS material.

The absorbent core 9 in FIG. 1A has a first absorbent layer 20 and a second absorbent layer 21. The second absorbent layer 21 is placed below the first absorbent layer 20. The first absorbent layer 20 is smaller than the second absorbent layer 21. The second absorbent layer 21 extends further forward and rearward in the absorbent product than the first absorbent layer 20.

However, the absorbent core may also comprise only one single layer or may comprise one or more further absorbent layers. The size of the different layers may also vary, and the absorbent core 9 described in FIGS. 1A and 1B is only one illustration of an absorbent core.

In FIG. 1B a cross-sectional view of the absorbent pad of FIG. 1A is shown, along the line II-II. The pad has a liquid permeable top sheet 24, a liquid impermeable back sheet 8, and an absorbent core 9 enclosed between the top sheet 24 and the back sheet 8 and an acquisition and distribution material 1 is located between the topsheet 24 and the absorbent core 9.

Figure 2:
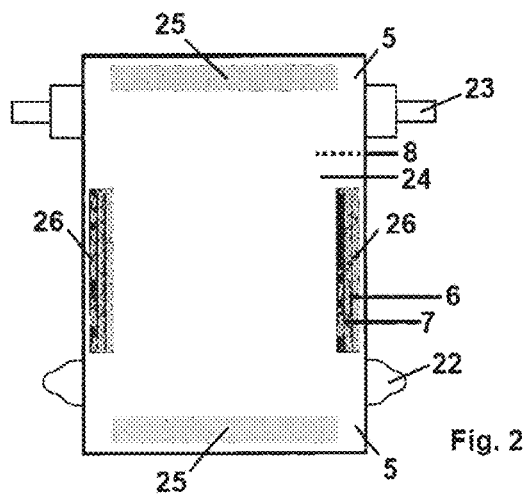
FIG. 2 is a top view of a diaper with PCM zones according to a preferred embodiment.
Figure 3:
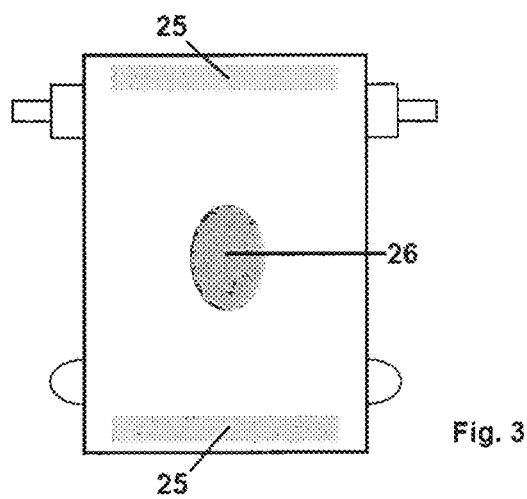
FIG. 3 is a top view of a diaper with PCM zones according to a preferred embodiment.
Figure 4:
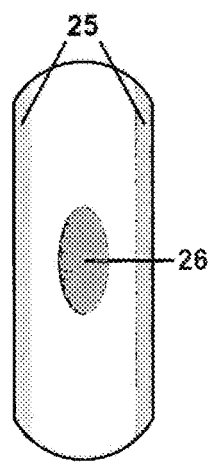
FIG. 4 is a top view of a pad with PCM zones according to a preferred embodiment.
Figure 5:
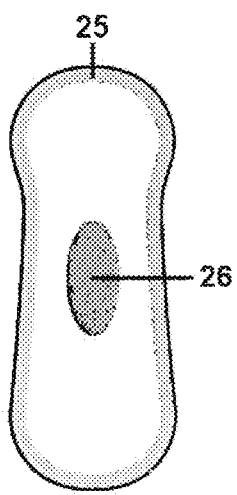
FIG. 5 is a top view of a pad with PCM zones according to a preferred embodiment.
Figure 6:
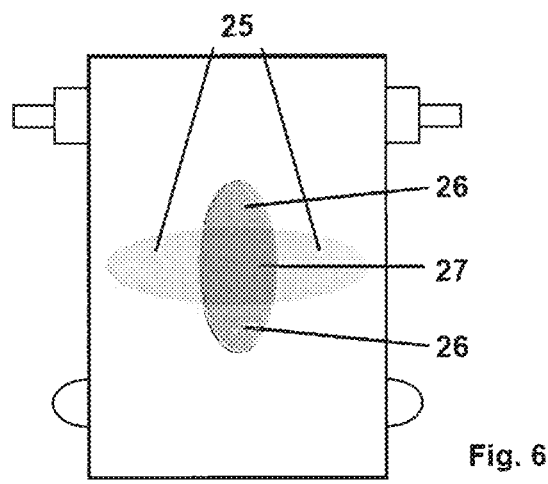
FIG. 6 is a top view of a diaper with PCM zones according to a preferred embodiment.

FIGS. 2-6 are illustrations of the absorbent articles further described in the Examples below. FIGS. 4 and 5 disclose pads. FIGS. 2, 3 and 6 disclose open tape type diapers having features known to the skilled man in the art and herein only described briefly. In FIG. 2 a diaper is depicted having a topsheet 24 and a backsheet 8, front and back waist areas 5, leg cuffs 6, standing gathers 7, grip tabs 22 and fastening tabs 23.

EXAMPLES

Example 1

Microencapsulated PCM was added in two zones by printing with flexographic printing on a material for a baby open diaper. The first zone was the waist area of the diaper according to area 25 in FIG. 2 and the second zone was the leg cuffs according to area 26 in FIG. 2. The phase change interval of the PCM was 30-40° C. (Thermusol HD32SE, Salca BV, melting point 32° C.) to balance the temperature rise occurring when the baby moves around. Different concentration of the microencapsulated PCM was added in the zones. The concentration of PCM in the waist area was 1 g/m2 and the concentration on the leg cuffs was 0.6 g/m2.

Example 2

Microencapsulated PCM was added in two zones by printing on a material for an adult incontinence diaper. The first zone was the waist area according to area 25 in FIG. 3 wherein PCM with a phase change interval of 25-35° C. was used (Micronal 5428X slurry, Microtek laboratories, melting point 28° C.) to balance the temperature on the individual when lying in bed with bedding on. The second zone was the wetness area in the crotch portion according to area 26 in FIG. 3 wherein PCM with a phase change interval of 35-40° C. (MPCM37 wet cake, Microtek laboratories, melting point 37° C.) to balance the temperature when the urine is cooling down and avoid discomfort after the wetting incident but before change of absorbent article. The concentration of PCM in the waist area was 4.6 g/m2 and the concentration in the wetness area was 1.5 g/m2.

Example 3

A PCM mixture with temperature interval of 30-40° C. (MPCM32 wet cake, Microtek laboratories, melting point 32° C. and MPCM37 wet cake, Microtek laboratories, melting point 37° C.) was added by printing on a material for a feminine pad with the first zone located along the longitudinal side portions according to area 25 in FIG. 4 to balance increased temperature when sweating. To the second zone, located in the wetness area according to area 26 in FIG. 4, PCM with a temperature interval of 35-40° C. (MPCM37 wet cake, Microtek laboratories, melting point 37° C.) was added to avoid discomfort of first increase in temperature when menstrual fluid or urine is warm (directly from body). The concentration of PCM in the first area was 1.8 g/m2 and the concentration in the wetness area was 0.3 g/m2.

Example 4

Microencapsulated PCM was added in two zones by printing on a material for an incontinence pad with a main first zone according to area 25 in FIG. 5 with an outer shape following the contour of the product and a uniform pattern with a constant concentration of 0.7 g/m2 PCM (Nextek 28, Microtek laboratories, melting temperature 28° C.). A second zone according to area 26 in FIG. 5 with the same PCM in a lower concentration of 0.4 g/m2 is in the wetting zone of the pad.

Example 5

A diaper with three zones of microencapsulated PCM added by flexographic printing, containing a combination of different PCMs and concentrations. The first zone is in a transverse zone according to area 25 in FIG. 6 and includes 1 g/m2 of the encapsulated PCM material ClimSel 32, Climator, temp interval 29-32° C. The second zone is a longitudinal portion according to area 26 in FIG. 6, partly overlapping with the first zone, with a PCM concentration of 3 g/m2 of MPCM32 wet cake, Microtek laboratories (temp interval 30-35° C.). The third zone will have a combined PCM concentration of 4 g/m2 and is located where the first and second zones overlap, according to area 27 in FIG. 6. The overlapping zones form a micropattern allowing for tailor made breathability.

The invention claimed is:

1. An absorbent article comprising at least a nonwoven topsheet layer and a backsheet layer, each layer having a body facing surface and a garment facing surface, and longitudinal and transversal edges, the article having a longitudinal front portion, a longitudinal back portion and a crotch portion located between the front and the back portion,
   the article comprising:
   a first zone and a second zone of microencapsulated reversible temperature-regulating phase change material (PCM) in non-breakable microcapsules on a surface of a layer of the article,
   wherein the first zone includes:
   a different non-breakable microencapsulated reversible temperature-regulating phase change material than what is in the second zone;
   a different concentration of non-breakable microencapsulated reversible temperature-regulating phase change material than what is in the second zone; or
   a non-breakable microencapsulated reversible temperature-regulating phase change material having different phase change temperature intervals than what is in the second zone,
   wherein the first and second zones have different boundaries, wherein the first zone includes two first end portions and a first middle portion between the two first end portions, wherein the second zone includes two second end portions and a second middle portion between the two second end portions, wherein the two first end portions are non-overlapping with the two second end portions, and wherein the first middle portion and the second middle portion overlap one another.

2. The absorbent article according to claim 1, wherein the second zone is more than 0% and less than 100% of the surface area of the layer.

3. The absorbent article according to claim 1, wherein the first zone of microencapsulated phase change material has a phase change transition temperature within 10-50° C.

4. The absorbent article according to claim 1, wherein the second zone of microencapsulated phase change material has a phase change transition temperature within 10-50° C.

5. The absorbent article according to claim 1, wherein the first zone is at least partly surrounded by the second zone of microencapsulated phase change material.

6. The absorbent article according claim 1, wherein the first and second zones are at least partly overlapping.

7. The absorbent article according to claim 1, wherein the second zone forms a micropattern within at least a part of the first zone.

8. The absorbent article according to claim 1, comprising a plurality of zones of microencapsulated PCM.

9. The absorbent article according to claim 1, wherein the concentration of PCM in the zones is >0.01<17 g/m$^2$.

10. The absorbent article according to claim 1, wherein the concentration of microcapsules in the first zone is 0.01-5.0 g/m$^2$.

11. The absorbent article according to claim 1, wherein the concentration of microcapsules in the second zone is 0.01-5.0 g/m$^2$.

12. The absorbent article according to claim 1, wherein the first zone is in a wetness zone of the article.

13. The absorbent article according to claim 12, wherein the second zone is outside the wetness zone but inside the crotch portion of the article.

14. The absorbent article according to claim 1, wherein the microencapsulated phase change material is located on any of the surfaces of the topsheet layer.

15. The absorbent article according to claim 1, wherein the article further comprises an intermediate layer having a body facing surface and a garment facing surface and wherein the microencapsulated phase change material is located on a surface of the intermediate layer.

16. The absorbent article according to claim 1, wherein at least the first zone has a non-linear boundary in at least a transversal direction of the article.

17. The absorbent article according to claim 16, wherein the non-linear boundary is obtained by a synchronized in-line printing technique.

18. The absorbent article according to claim 1, wherein the article is configured such that, when worn by a wearer, a first portion of the article confronts a first portion of the wearer having a first average temperature, and a second portion of the article confronts a second portion of the wearer having a second average temperature that is higher than the first average temperature, and the first zone is located in the first portion of the article and the second zone is located in the second portion of the article.

19. The absorbent article according to claim 1, wherein one of the first and second zones is a transverse zone with a major axis extending in a transverse direction, and the other one of the first and second zones is a longitudinal zone with a major axis extending in a longitudinal direction.

20. A method of applying reversible temperature-regulating phase change material (PCM) to an absorbent article comprising at least a nonwoven topsheet layer and a backsheet layer, each layer having a body facing surface and a garment facing surface and longitudinal and transversal edges, the article having a longitudinal front portion, a longitudinal back portion and a crotch portion located between the front and the back portion, the method comprising the steps of:

printing a first zone and a second zone of non-breakable microencapsulated phase change material on a surface of a layer of the article, wherein the first zone includes:

a different non-breakable microencapsulated reversible temperature-regulating phase change material than what is in the second zone;

a different concentration of non-breakable microencapsulated reversible temperature-regulating phase change material than what is in the second zone; or a non-breakable microencapsulated reversible temperature-regulating phase change material having different phase change temperature intervals than what is in the second zone, wherein the first and second zones have different boundaries, wherein the first zone includes two first end portions and a first middle portion between the two first end portions, wherein the second zone includes two second end portions and a second middle portion between the two second end portions, wherein the two first end portions are non-overlapping with the two second end portions, and wherein the first middle portion and the second middle portion overlap one another.

21. The method of applying PCM according to claim 20, wherein printing is by means of an in-line synchronized print technique.

22. The method of applying PCM according to claim 21, wherein the in- line synchronized print technique is a flexographic printing technique.

23. The method of applying PCM according to claim 20, wherein the article is configured such that, when worn by a wearer, a first portion of the article confronts a first portion of the wearer having a first average temperature, and a second portion of the article confronts a second portion of the wearer having a second average temperature that is higher than the first average temperature, and the first zone is located in the first portion of the article and the second zone is located in the second portion of the article.

24. The method of applying PCM according to claim 20, wherein one of the first and second zones is a transverse zone with a major axis extending in a transverse direction, and the other one of the first and second zones is a longitudinal zone with a major axis extending in a longitudinal direction.

25. An absorbent article comprising at least a nonwoven topsheet layer and a backsheet layer, each layer having a body facing surface and a garment facing surface, and longitudinal and transversal edges, the article having a longitudinal front portion, a longitudinal back portion and a crotch portion located between the front and the back portion, the article comprising:

a first zone and a second zone of microencapsulated reversible temperature-regulating phase change material (PCM) in non-breakable microcapsules on a surface of a layer of the article, wherein the first zone includes:

a different non-breakable microencapsulated reversible temperature-regulating phase change material than what is in the second zone;

a different concentration of non-breakable microencapsulated reversible temperature-regulating phase change material than what is in the second zone; or a non-breakable microencapsulated reversible temperature-regulating phase change material having different phase change temperature intervals than what is in the second zone, wherein the first and second zones have different boundaries and are non-overlapping.

26. The absorbent article according to claim 25, wherein a main axis of one of the first or second zone extends along contour of the absorbent article.

27. The absorbent article according to claim 25, wherein a main axis of one of the first or second zone extends along one of the longitudinal or transversal edges.

28. The absorbent article according to claim 25, wherein a main axis of one of the first or second zone extends perpendicularly to a main axis of the other one of the first or second zone.

29. A method of applying reversible temperature-regulating phase change material (PCM) to an absorbent article comprising at least a nonwoven topsheet layer and a backsheet layer, each layer having a body facing surface and a garment facing surface and longitudinal and transversal edges, the article having a longitudinal front portion, a longitudinal back portion and a crotch portion located between the front and the back portion, the method comprising the steps of:

printing a first zone and a second zone of non-breakable microencapsulated phase change material on a surface of a layer of the article, wherein the first zone includes:

a different non-breakable microencapsulated reversible temperature-regulating phase change material than what is in the second zone;

a different concentration of non-breakable microencapsulated reversible temperature-regulating phase change material than what is in the second zone; or a non-breakable microencapsulated reversible temperature-regulating phase change material having different phase change temperature intervals than what is in the second zone, wherein the first and second zones have different boundaries and are non-overlapping.

30. The method according to claim 29, wherein a main axis of one of the first or second zone extends along contour of the absorbent article.

31. The method according to claim 29, wherein a main axis of one of the first or second zone extends along one of the longitudinal or transversal edges.

32. The method according to claim 29, wherein a main axis of one of the first or second zone extends perpendicularly to a main axis of the other one of the first or second zone.

* * * * *